United States Patent
Oura et al.

(10) Patent No.: US 9,708,578 B2
(45) Date of Patent: Jul. 18, 2017

(54) MEASURING UNIT TO BE ATTACHED TO CELL CULTURE CONTAINER, CELL CULTURE CONTAINER, AND CULTIVATION CONDITION MONITORING SYSTEM

(71) Applicants: NIHON KOHDEN CORPORATION, Tokyo (JP); TOKYO WOMEN'S MEDICAL UNIVERSITY, Tokyo (JP)

(72) Inventors: Mitsuhiro Oura, Tokyo (JP); Hirotsugu Kubo, Tokyo (JP); Katsuyoshi Suzuki, Tokyo (JP); Katsuhide Tone, Tokyo (JP); Teruo Okano, Tokyo (JP); Tatsuya Shimizu, Tokyo (JP)

(73) Assignees: NIHON KOHDEN CORPORATION, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 1047 days.

(21) Appl. No.: 13/835,042

(22) Filed: Mar. 15, 2013

(65) Prior Publication Data
US 2013/0260445 A1    Oct. 3, 2013

(30) Foreign Application Priority Data
Mar. 29, 2012   (JP) ................... 2012-077785

(51) Int. Cl.
*C12M 1/34*   (2006.01)
*C12M 1/36*   (2006.01)

(52) U.S. Cl.
CPC .......... *C12M 41/46* (2013.01); *C12M 41/00* (2013.01); *C12M 41/48* (2013.01)

(58) Field of Classification Search
CPC ...... C12M 41/46; C12M 41/48; C12M 41/00; C12M 23/04; A61B 5/7203; A61B 5/14551; A61B 5/7257; A61B 2560/0209
See application file for complete search history.

(56) References Cited

U.S. PATENT DOCUMENTS

| 2006/0057710 A1 | 3/2006 | Ishiura et al. |
| 2006/0201580 A1 | 9/2006 | Kang |
| 2006/0252608 A1 | 11/2006 | Kang et al. |

(Continued)

FOREIGN PATENT DOCUMENTS

| JP | 2005-143371 A | 6/2005 |
| JP | 2006-6261 A | 1/2006 |

(Continued)

OTHER PUBLICATIONS

European Office Action for the related European Patent Application No. 13 159 383.2 dated Oct. 6, 2015.

(Continued)

*Primary Examiner* — William H Beisner
*Assistant Examiner* — Danielle Henkel
(74) *Attorney, Agent, or Firm* — Kenealy Vaidya LLP

(57) ABSTRACT

A measuring unit which is to be attached to a cell culture container configured to accommodate cells to be cultured and a culture solution, includes: a measurer which is configured to measure information related to the cells and the culture solution, in a non-contact manner; and a sensor which is configured to detect at least one of a position, a posture, an impact, an orientation, and vibration.

5 Claims, 5 Drawing Sheets

(56) References Cited

U.S. PATENT DOCUMENTS

| | | | |
|---|---|---|---|
| 2006/0258515 A1 | 11/2006 | Kang et al. | |
| 2007/0286770 A1* | 12/2007 | Magnant | B01L 9/50 |
| | | | 422/400 |
| 2008/0318307 A1 | 12/2008 | Spittle et al. | |
| 2010/0009335 A1 | 1/2010 | Joseph et al. | |
| 2010/0277617 A1 | 11/2010 | Hollinger | |
| 2011/0207209 A1* | 8/2011 | Hammons | C12M 23/42 |
| | | | 435/297.1 |
| 2012/0262541 A1 | 10/2012 | Hollinger | |

FOREIGN PATENT DOCUMENTS

| | | |
|---|---|---|
| JP | 2007-93450 A | 4/2007 |
| JP | 2011-97878 A | 5/2011 |
| WO | 2006/099320 A2 | 9/2006 |
| WO | 2007/092571 A2 | 8/2007 |
| WO | 2007/120619 A2 | 10/2007 |
| WO | 2008/120614 A1 | 10/2008 |
| WO | 2011/090792 A1 | 7/2011 |

OTHER PUBLICATIONS

Japanese Office Action for the related Japanese Patent Application No. 2012-077785 dated Sep. 29, 2015.
Database WPI; Thomson Scientific, London, GB; AN 2007-548496; XP002698829.
The extended European Search Report for the related European Patent Application No. 13159383.2 dated Jun. 25, 2013.

* cited by examiner

MEASURING UNIT TO BE ATTACHED TO CELL CULTURE CONTAINER, CELL CULTURE CONTAINER, AND CULTIVATION CONDITION MONITORING SYSTEM

CROSS-REFERENCE TO RELATED APPLICATION(S)

This application is based upon and claims the benefit of priority from prior Japanese patent application No. 2012-077785, filed on Mar. 29, 2012, the entire contents of which are incorporated herein by reference.

BACKGROUND

The presently disclosed subject matter relates to a cell culture container which is configured to accommodate cells to be cultured and a culture solution, a measuring unit which is attached to the cell culture container to measure information related to the cells and the culture solution, and a system for monitoring the cultivation condition of the cells.

As a cell culture container of this kind, there is a container which is used in regenerative medicine or culture of cells such as an artificially fertilized cell (for example, see JP-A-2006-6261). Such a cell culture container is stored in an incubator in which, for example, the temperature and the concentration of carbon dioxide are controlled.

Vibration or displacement which is applied to a cell culture container during culture may affect the cultivation condition of cells, and therefore is requested to be avoided as far as possible. However, it is usual that a particular countermeasure against to vibration is not taken in an incubator. In the case where a difference between cultivation conditions is noted, therefore, it is difficult to determine whether the difference is caused by vibration applied during the culture process, or due to another factor. Moreover, there is a possibility that vibration or stimulation may be applied to a cell culture container due to a low skill level of the operator in an exchange of the culture medium or the like.

SUMMARY

The presently disclosed subject matter may provide a technique for detecting a fact that vibration was applied to or displacement occurred in a cell culture container during the culture process, enabling the detection result to be used in analysis of the cultivation condition, and objectively evaluating the skill level of the operator.

There is provided a measuring unit. The measuring unit which is to be attached to a cell culture container configured to accommodate cells to be cultured and a culture solution, the measuring unit may comprise: a measurer which is configured to measure information related to the cells and the culture solution, in a non-contact manner; and a sensor which is configured to detect at least one of a position, a posture, an impact, an orientation, and vibration.

The sensor may be one of an acceleration sensor, a gyro sensor, a geomagnetic sensor, an impact sensor, an orientation sensor, a magnetic position sensor, and a GPS sensor.

The measurer may measure, as the information, at least one of a pH of the culture solution, a temperature of the culture solution, a concentration of carbon dioxide in a periphery of the culture solution, a concentration of oxygen in a periphery of the culture solution, a partial pressure of oxygen in a periphery of the culture solution, a concentration of ammonia in a periphery of the culture solution, a concentration of glucose of a culture solution, and a concentration of lactate of the culture solution.

The measuring unit may be attachable to and detachable from the cell culture container.

The measuring unit may further comprise a storage which is configured to store data indicating a result of detection by the sensor while correlating the result with time information.

There is provided a cell culture container. The cell culture container may comprise: a culture cell accommodator which is configured to accommodate cells to be cultured and a culture solution; a measuring unit accommodator which is configured to accommodate a measuring unit that is configured to measure information related to the cells and the culture solution, in a non-contact manner; and a sensor which is configured to detect at least one of a position, a posture, an impact, an orientation, and vibration.

The sensor may be one of an acceleration sensor, a gyro sensor, a geomagnetic sensor, an impact sensor, an orientation sensor, a magnetic position sensor, and a GPS sensor.

The cell culture container may further comprise a storage which is configured to store data indicating a result of detection by the sensor while correlating the result with time information.

The cell culture container may further comprise a communicator which is configured to wirelessly transmit data indicating a result of detection by the sensor.

There is provided a cultivation condition monitoring system. The cultivation condition monitoring system may comprise: a cell culture container which is configured to accommodate cells to be cultured and a culture solution; a measuring unit which is attached to the cell culture container, and which is configured to measure information related to the cells and the culture solution, in a non-contact manner; a sensor which is disposed in one of the cell culture container and the measuring unit, and which is configured to detect at least one of a position, a posture, an impact, an orientation, and vibration; a communicator which is disposed in one of the cell culture container and the measuring unit, and which is configured to wirelessly transmit data indicating a result of detection by the sensor; and a communicating apparatus which is configured to wirelessly acquire the data from the communicator.

The cultivation condition monitoring system may further comprise a warning generator which, when the data satisfy a predetermined condition, is configured to generate warning.

The cultivation condition monitoring system may further comprise a history information producer which is configured to produce history information of a cultivation condition based on the data.

The cultivation condition monitoring system may further comprise an evaluation information producer which is configured to produce evaluation information of a cultivation skill based on the data.

The cultivation condition monitoring system may further comprise an incubator which is configured to accommodate the cell culture container, and the communicating apparatus may be disposed in the incubator.

The cultivation condition monitoring system may further comprise: a transporting mechanism which is configured to automatically place the cell culture container at a predetermined position in the incubator; and a control information producer which is configured to produce information for controlling the transporting mechanism, based on the data.

DETAILED DESCRIPTION OF EXEMPLARY EMBODIMENTS

Figure 1:
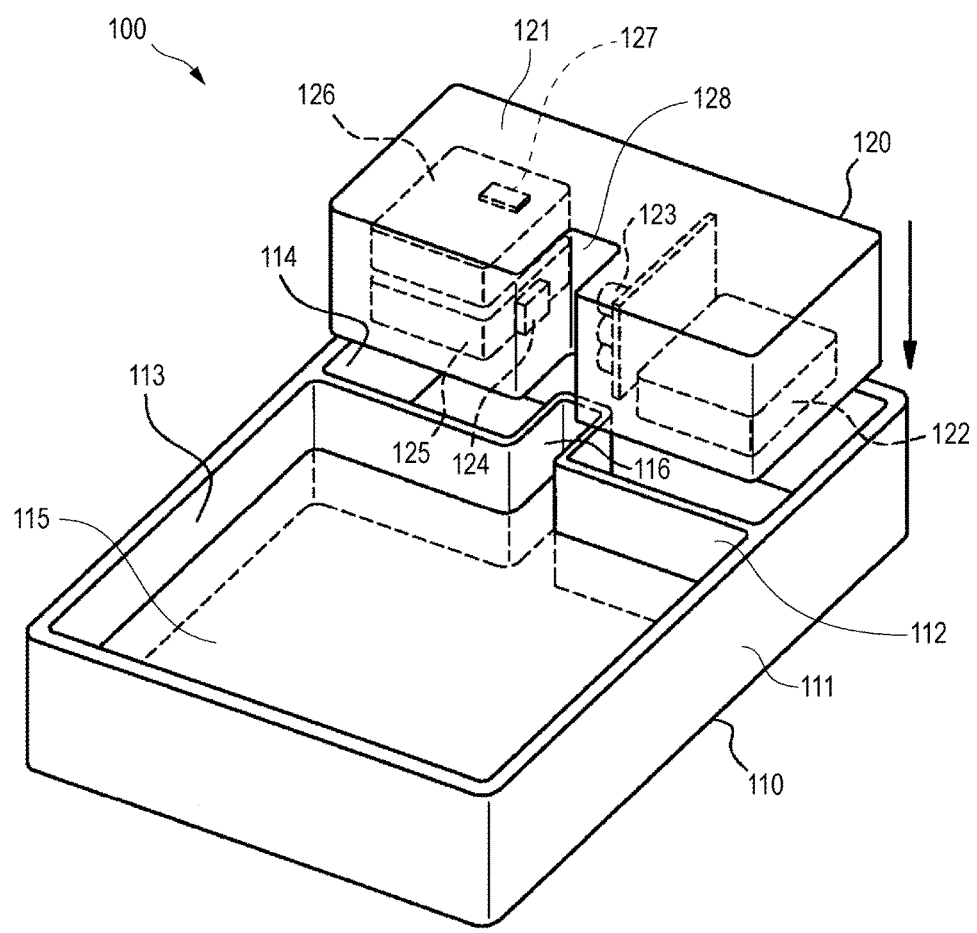
FIG. 1 is an exploded perspective view showing a cell incubator in a first embodiment of the presently disclosed subject matter.

Hereinafter, embodiments of the presently disclosed subject matter will be described with reference to the accompanying drawings. In the drawings which will be referenced in the following description, the scale is adequately changed in order to draw components in a recognizable size.

FIG. 1 is an exploded perspective view showing a cell incubator 100 in a first embodiment of the presently disclosed subject matter. The cell incubator 100 is configured by a cell culture container 110 and a measuring unit 120.

The cell culture container 110 includes: a peripheral wall 111; a culture cell accommodator 113 which is partitioned by a partition wall 112; and a measurement unit accommodator 114. The culture cell accommodator 113 forms a space for accommodating cells to be cultured and a culture solution 115. The measuring unit 120 is attachable to and detachable from the cell culture container 110, and inserted into the measurement unit accommodator 114 in the direction indicated by the arrow. A part of the partition wall 112 is projected toward the measurement unit accommodator 114 to form a convex portion 116.

The measuring unit 120 is an apparatus for measuring the pH of the culture solution 115. The measuring unit 120 includes a housing 121, a battery 122, a light emitter 123, a light receiver 124, a controller 125, a communicator 126, and an acceleration sensor 127. A concave portion 128 having a shape corresponding to that of the convex portion 116 of the cell culture container 110 is formed in a part of the housing 121. The light emitter 123 and the light receiver 124 are opposed to each other across the concave portion 128.

In the partition wall 112 of the cell culture container 110, at least the portion where the convex portion 116 is formed is transparent to light emitted from the light emitter 123. When the measuring unit 120 is accommodated in the measurement unit accommodator 114, the light emitter 123 and the light receiver 124 are opposed to each other across the partition wall which forms the convex portion 116.

The battery 122 supplies a driving power to the elements constituting the measuring unit 120. The controller 125 includes a calculating device and memory which are not shown, and controls the operations of the elements constituting the measuring unit 120.

The light emitter 123 includes three LEDs which respectively emit light at different wavelengths. The light emitted from the LEDs pass through the culture solution 115 in the convex portion 116 to be received by the light receiver 124. The light receiver 124 is configured by a photodiode so as to output a signal corresponding to the intensity of the received light.

The culture solution 115 accommodated in the culture cell accommodator 113 contains a pH indicator. One of the three LEDs is a calibration light source which emits light at a wavelength that shows a very little absorption by the pH indicator. One of the other two LEDs is a light source which emits light at a wavelength that shows a more conspicuous absorption by the indicator as the pH of the culture solution 115 moves further toward the acidic side of the median value of a predetermined management width, and the other LED is a light source which emits light at a wavelength that shows a more conspicuous absorption by the indicator as the pH of the culture solution 115 moves further toward the alkaline side of the median value.

In the embodiment, phenol red is used as the indicator. In this case, the LED which functions as the calibration light source emits light in a 700 nm band, and the remaining two LEDs emit light in 558 nm and 430 nm bands.

When the pH of the culture solution 115 is to be measured, the calibration LED is first caused to emit light, and a calibration coefficient of the absorption by the culture solution 115 is obtained. Next, the remaining two LEDs are caused to alternately emit light, and the absorbances by the culture solution 115 at the wavelengths are measured.

The controller 125 determines the pH of the culture solution 115 based on previously obtained relationships in the indicator between the pH and the absorbance, and the calibration coefficient. Then, the data indicating the determined pH (pH data) are stored into the memory of the controller 125 while being correlated with information indicative of the measurement time.

Namely, the light emitter 123, the light receiver 124, and the controller 125 function as the measurer in the presently disclosed subject matter which measures the pH as information related to the culture solution 115, in a non-contact manner.

For example, the acceleration sensor 127 which functions as the sensor in the presently disclosed subject matter is a three-axis acceleration sensor. When accelerations in the XYZ directions are detected, it is possible to detect the posture of the measuring unit 120. Since the measuring unit 120 is attached to the cell culture container 110, the posture detection can be deemed to detect the posture of the cell culture container 110. When the posture is detected, also a fact that vibration or an impact was applied to the cell incubator 100 can be detected.

The data indicating the result of the detection by the acceleration sensor 127 (posture data) are stored into the memory of the controller 125 while being correlated with information indicative of the detection time. In this case, the memory functions as the storage in the presently disclosed subject matter.

Figure 2:
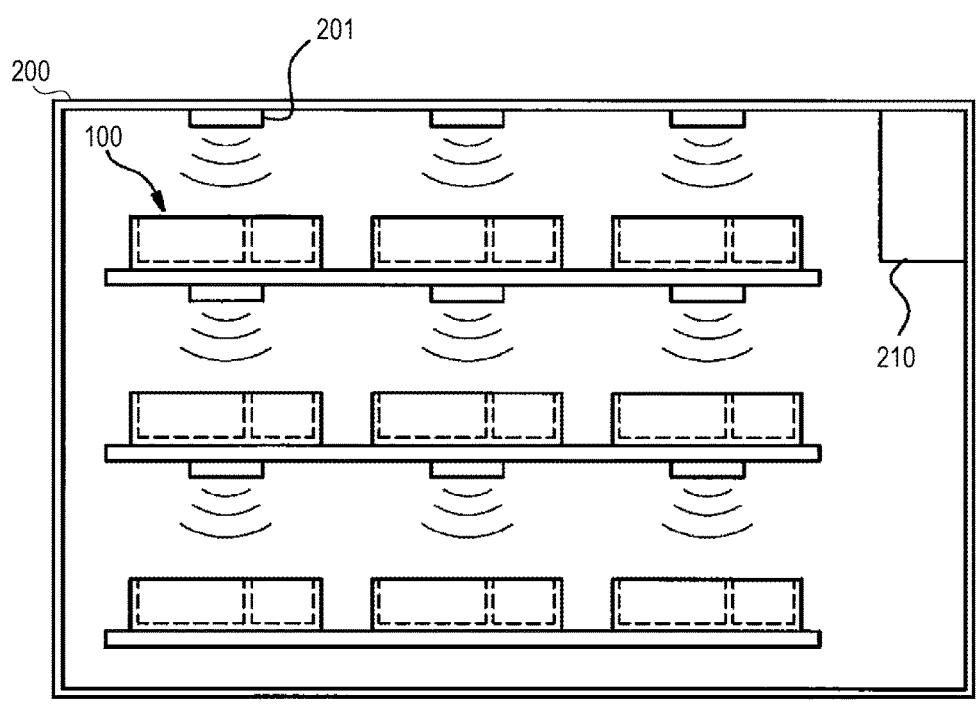
FIG. 2 is a view diagrammatically showing an incubator into which the cell incubator of FIG. 1 is accommodated.

As shown in FIG. 2, the cell incubator 100 is stored in an incubator 200, and culture of cells is performed. The incubator 200 is configured so as to be able to accommodate a plurality of cell incubators 100.

Figure 3:
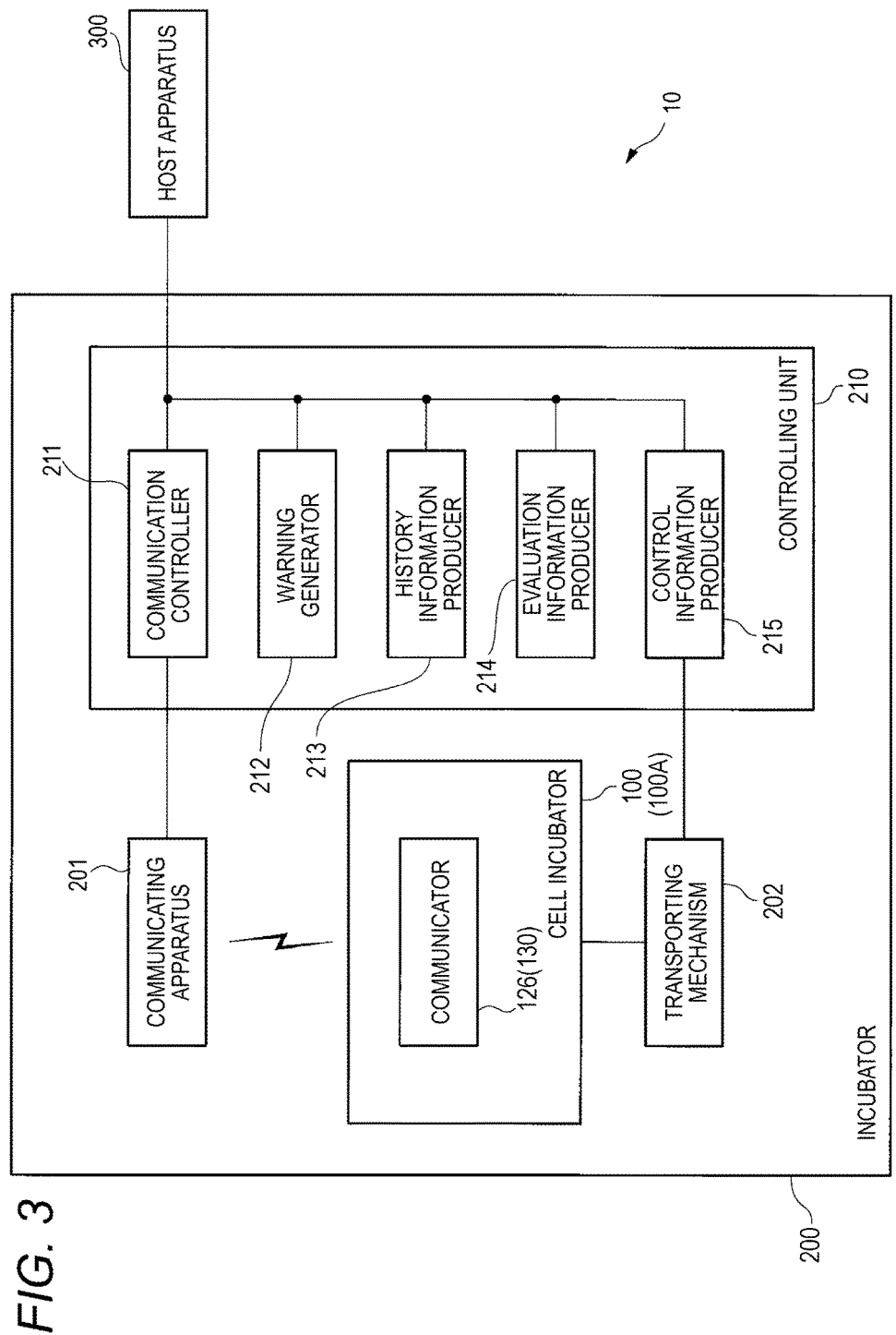
FIG. 3 is a block diagram illustrating the function of a controlling unit in the incubator of FIG. 2.

As shown in FIG. 3, the incubator 200 includes communicating apparatuses 201, a transporting mechanism 202, and a controlling unit 210. The transporting mechanism 202 is a mechanism which automatically transports each of the plurality of cell incubators 100 to a predetermined position. As shown in FIG. 2, in the incubator 200, the plurality of communicating apparatuses 201 are placed so as to correspond to the plurality of cell incubators 100 which are placed at predetermined positions, respectively.

The communicator 126 of the measuring unit 120 is configured so as to wirelessly transmit the pH data and posture data stored in the memory of the controller 125, to corresponding one of the communicating apparatuses 201.

The controlling unit 210 includes a communication controller 211, a warning generator 212, a history information producer 213, an evaluation information producer 214, and a control information producer 215. The controlling unit 210 is communicably connected to a host apparatus 300 such as a computer via the communication controller 211. The cell incubator 100, the incubator 200, and the host apparatus 300 constitute a cultivation condition monitoring system 10.

The communication controller 211 controls wireless communication performed between the communicator 126 of the measuring unit 120 and the communicating apparatuses 201 of the incubator 200, and acquires the pH data and the posture data from the measuring unit 120 via the wireless communication. Since wireless communication is used, the data can be acquired without applying vibration to the cell incubator 100.

The warning generator 212 is configured so as to generate warning in the case where the posture data acquired by the communication controller 211 satisfy a predetermined condition. The warning is issued in the case where the posture data indicate that the cell incubator 100 is placed in an inclined state in the incubator 200, or that excessive vibration or impact was caused to be applied to the cell incubator 100 by handling performed in an operation in which the operator took out the cell incubator 100 from the incubator 200 in order to replace the medium. The notification of warning is performed by at least one of audio and visual means. When the cell incubator 100 from which the warning originates is replaced with another one or its posture is corrected, it is possible to eliminate the possibility that the culture of cells progresses under undesirable conditions.

The history information producer 213 is configured so as to produce history information for each of the pH data and posture data acquired by the communication controller 211. As described above, each of the pH data and the posture data is correlated with information indicative of the measurement time or the detection time, and therefore history information can be easily produced. In evaluation of the cultivation condition, it is possible to perform analysis correlated with the posture of the cell incubator, and the presence or absence of applied vibration or impact during the culture process.

The evaluation information producer 214 is configured so as to produce evaluation information of the cultivation skill based on the pH data and posture data acquired by the communication controller 211, or the history information. The acceleration sensor 127 of the measuring unit 120 can detect the posture of the cell incubator 100 and vibration applied thereto, not only during the period when the cell incubator 100 is stored in the incubator 200, but also during the period when the operator prepares a medium or carries the container. From the record of the unit, therefore, the cultivation technique (skill) of the operator can be objectively evaluated. Evaluation results can be used in, for example, an operator training tool for improving skills to stably obtain a cultivation result.

The control information producer 215 is configured so as to produce information for controlling the operation of the transporting mechanism 202 by using at least one of the posture data acquired by the communication controller 211, the warning issued from the warning generator 212, the history information produced by the history information producer 213, and the evaluation information produced by the evaluation information producer 214. For example, the cell incubator 100 from which the warning originates can be replaced with another one, its posture can be corrected, or, based on the history information and the evaluation information, the transporting speed can be adjusted in order to suppress vibration.

The communication controller 211 controls also communication performed between the controlling unit 210 and the host apparatus 300. The communication controller 211 is configured so as to, in accordance with instructions supplied from the side of the host apparatus 300, control the operations of the various elements of the incubator 200, and transmit various data and information acquired or produced in the controlling unit 210, toward the host apparatus 300. In the side of the host apparatus 300, the above-described analysis and evaluation are performed based on the history information and evaluation information acquired from the controlling unit 210.

As described above, according to the configuration of the embodiment, the posture or vibration of the cell incubator 100 which may affect the cultivation condition of cells can be detected, and an adequate control, and analysis and evaluation of the cultivation condition in which the detection result is used are enabled.

The used cell culture container 110 will be disposed. The measuring unit 120 including the acceleration sensor 127 is attachable to and detachable from the cell culture container 110. Therefore, the configuration can be reused and is economical.

Figure 4:
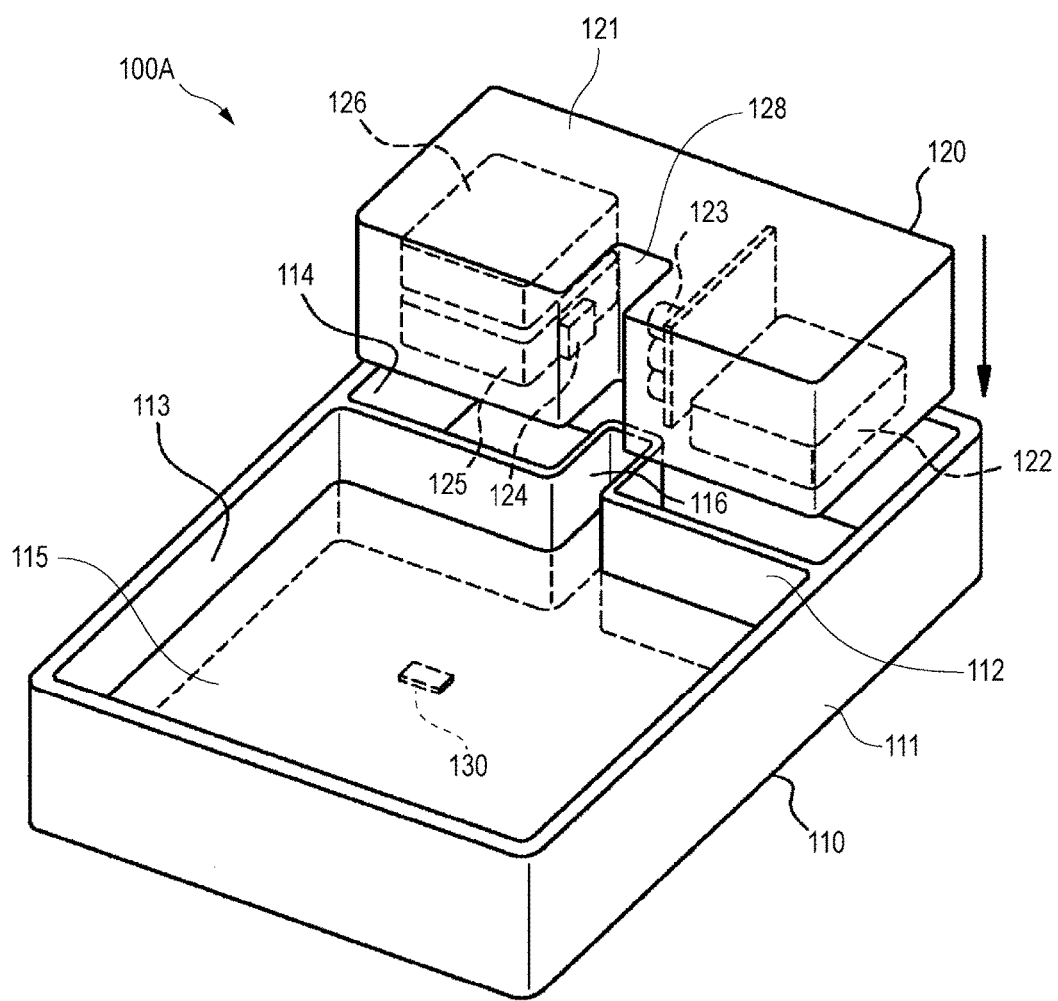
FIG. 4 is an exploded perspective view showing a cell incubator in a second embodiment of the presently disclosed subject matter.

Next, a cell incubator 100A in a second embodiment of the presently disclosed subject matter will be described with reference to FIG. 4. Components which are identical with or equivalent to those of the cell incubator 100 in the first embodiment are denoted by the same reference numerals, and duplicated description is omitted.

Figure 5:
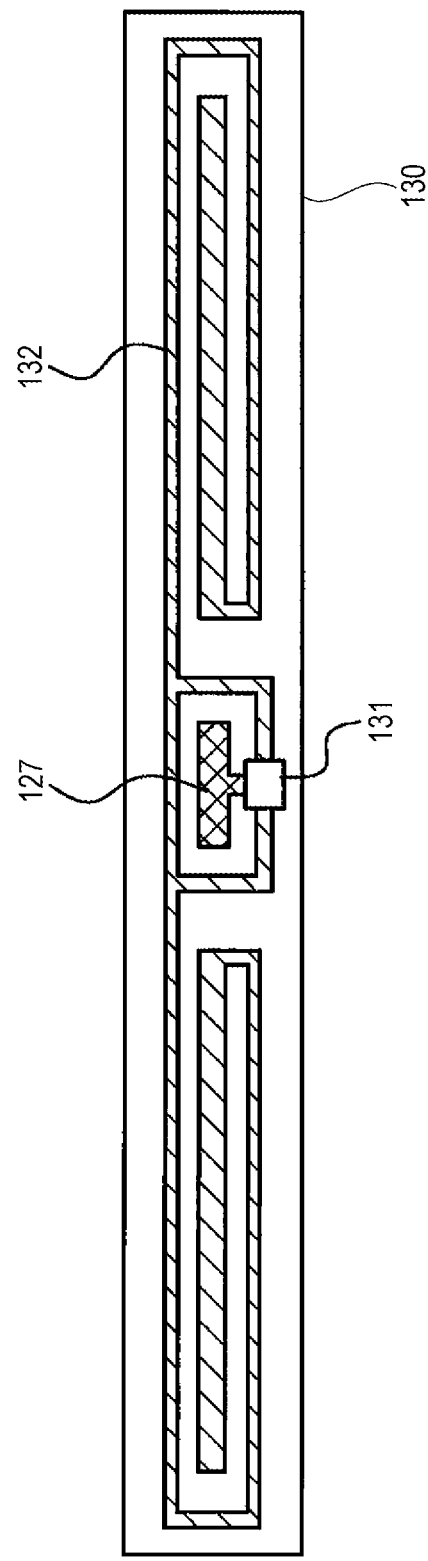
FIG. 5 is a view diagrammatically showing the configuration of an RFID tag in the cell incubator of FIG. 4.

The cell incubator 100A is different from the cell incubator 100 in that the acceleration sensor 127 is disposed in the cell culture container 110. Specifically, the acceleration sensor 127 is incorporated in an RFID tag 130 attached to a bottom portion of the cell culture container 110. As shown in the internal structure of FIG. 5, the RFID tag 130 includes an IC chip 131 and an antenna 132 in addition to the acceleration sensor 127.

The acceleration sensor 127 receives a power supply from the IC chip 131, and can detect the posture of the cell culture container 110. The IC chip 131 includes a memory which stores the result of the detection by the acceleration sensor 127 (posture data) while correlating the result with information indicative of the measurement time. In the embodiment, the IC chip 131 functions as the storage in the presently disclosed subject matter.

The IC chip 131 is configured so that it can wirelessly transmit the posture data stored in the memory through the antenna 132 to the communicating apparatuses 201 disposed in the incubator 200. In the embodiment, namely, the RFID tag 130 functions as the communicator in the presently disclosed subject matter.

The communication controller 211 of the controlling unit 210 of the incubator 200 controls wireless communication performed between the RFID tag 130 and the communicating apparatuses 201, and acquires the posture data from the RFID tag 130 via the wireless communication. The posture data are handled in a similar manner as those in the first embodiment, and therefore detailed description is omitted.

When the acceleration sensor 127 is disposed in the cell culture container 110 as in the embodiment, the posture and vibration can be detected in a place which is closer to the medium, and it is possible to know more correctly the culture process.

The RFID tag 130 will be disposed together with the used cell culture container 110. When the RFID tag 130 is configured so as to be attachable to and detachable from the cell culture container 110, however, the acceleration sensor 127 can be reused.

The embodiments have been described in order to facilitate understanding of the presently disclosed subject matter, and are not intended to limit the presently disclosed subject matter. It is a matter of course that the presently disclosed subject matter may be changed or improved without departing the spirit thereof, and includes equivalents thereof.

As the sensor which detects the posture of the cell incubator 100, a gyro sensor, geomagnetic sensor, orientation sensor, or impact sensor may be used in place of the acceleration sensor 127. A configuration where the position of the cell incubator 100 is detected by using a GPS sensor or magnetic position sensor may be employed. Also when the position is detected, it is possible to detect a fact that vibration or an impact was applied to the cell incubator 100. Furthermore, it is possible to check when and how a process was performed on cultured cells. In the presently disclosed subject matter, by the sensor, at least one of the position, the posture, the impact, the vibration, and an orientation may be detected.

The measurement target of the measuring unit 120 is not limited to the pH of the culture solution. In addition to or in place of this, at least one of the temperature of the culture solution 115, the concentration of carbon dioxide in the periphery of the culture solution 115, the concentration of oxygen in the periphery of the culture solution 115, the partial pressure of oxygen in the periphery of the culture solution 115, the concentration of ammonia in the periphery of the culture solution 115, the concentration of glucose of the culture solution 115, and the concentration of lactate of the culture solution 115 may be used as information related to cells and the culture solution 115, and set as the measurement target. The position and configuration of the measurer may be adequately determined in accordance with the measurement target.

The timing when the communicating apparatuses 201 of the incubator 200 acquire the pH data and the posture data by means of wireless communication with the communicator 126 of the measuring unit 120, or that with the RFID tag 130 of the cell culture container 110 may be adequately determined. The data may be collectively acquired after the cultivation is ended, a configuration where the data are acquired at constant time intervals may be employed, or the data may be acquired in real time.

The acquisition of the pH data and the posture data from the communicator 126 of the measuring unit 120 or the RFID tag 130 of the cell culture container 110 is not always required to be performed by the communicating apparatuses 201 disposed in the incubator 200. For example, a configuration where wireless communication is performed through a communicating apparatus such as an RFID reader which is disposed outside the incubator 200 may be employed.

The acquisition of the pH data and the posture data through the communicator 126 of the measuring unit 120 is not always required to be performed via wireless communication. A configuration where, after the cultivation is ended, the measuring unit 120 detached from the cell culture container 110, and the host apparatus 300 are wire-connected through data communication terminals disposed in the measuring unit 120, and the pH data and the posture data are then transmitted to the host apparatus 300 may be employed.

A configuration where at least one of the warning generator 212, history information producer 213, evaluation information producer 214, and control information producer 215 which are disposed in the controlling unit 210 of the incubator 200 is disposed on the side of the host apparatus 300 may be employed.

According to as aspect of the presently disclosed subject matter, the posture or vibration which may affect the cultivation condition of cells can be detected, and an adequate control, and analysis and evaluation of the cultivation condition in which the detection result is used are enabled. Since wireless communication is used, data indicating the detection result can be acquired without applying vibration to the cell culture container.

According to as aspect of the presently disclosed subject matter, when the information indicating the cultivation condition is to be evaluated, analysis correlated with the displacement and posture of the cell culture container, and the presence or absence of applied vibration or impact is enabled.

According to as aspect of the presently disclosed subject matter, a used cell culture container will be disposed, but the measuring unit including a sensor can be reused. Therefore, the configuration is economical.

According to as aspect of the presently disclosed subject matter, history information of the culture process can be easily produced. The history information can be used in evaluation of the cultivation condition.

According to as aspect of the presently disclosed subject matter, the posture and vibration can be detected in a place which is closer to the medium, and it is possible to know more correctly the culture process.

According to as aspect of the presently disclosed subject matter, data indicating the detection result can be acquired without applying vibration to the cell culture container.

According to as aspect of the presently disclosed subject matter, a cell culture container from which the warning originates can be replaced with another one or its posture can be corrected, and therefore it is possible to eliminate the possibility that the culture of cells progresses under undesirable conditions.

According to as aspect of the presently disclosed subject matter, in evaluation of the cultivation condition, it is possible to perform analysis correlated with the posture of the cell incubator during the culture process, and the presence or absence of applied vibration or impact.

According to as aspect of the presently disclosed subject matter, based on the result of the detection of the posture of the cell incubator or vibration which is applied to the cell incubator when the operator prepares a medium or carries the container, it is possible to evaluate the cultivation skill of the operator.

According to as aspect of the presently disclosed subject matter, it is possible to suppress the possibility that, in acquisition of data indicating the result of detection by the sensor, vibration may be applied to the cell culture container.

According to as aspect of the presently disclosed subject matter, handling of the cell culture container by using the transporting mechanism can be automated in accordance with the result of detection by the sensor.

What is claimed is:
1. A cultivation condition monitoring system comprising:
a cell culture container which accommodates cells to be cultured and a culture solution;
a measuring unit which is attached to the cell culture container, and which measures information related to the cells and the culture solution, in a non-contact manner;
a sensor which is disposed in one of the cell culture container and the measuring unit, and which detects history information including at least one of a posture of the cell culture container and vibration applied to the cell culture container;

a communicator which is disposed in one of the cell culture container and the measuring unit, and which wirelessly transmits data indicating a result of detection by the sensor;

a communicating apparatus which wirelessly acquires the data from the communicator; and a history information producer comprising a controller configured to (i) record the history information and (ii) correlate the history information with at least one of a measurement time and a detection time.

2. The cultivation condition monitoring system according to claim 1, further comprising a warning generator which, when the data satisfy a predetermined condition, generates warning.

3. The cultivation condition monitoring system according to claim 1, further comprising an evaluation information producer which produces evaluation information of a cultivation skill based on the data.

4. The cultivation condition monitoring system according to claim 1, further comprising an incubator which accommodates the cell culture container, wherein the communicating apparatus is disposed in the incubator.

5. The cultivation condition monitoring system according to claim 4, further comprising:

a transporting mechanism which places the cell culture container at a predetermined position in the incubator; and a control information producer which produces information for controlling the transporting mechanism, based on the data.

* * * * *